United States Patent [19]

Arndt et al.

[11] 4,257,804
[45] Mar. 24, 1981

[54] CARBAMIC ACID ESTER, PROCESS FOR MAKING THE SAME AND COMPOSITION CONTAINING SAME

[75] Inventors: Friedrich Arndt; Ludwig Nüsslein, both of Berlin, Fed. Rep. of Germany

[73] Assignee: Schering Aktiengesellschaft, Berlin and Bergkamen, Fed. Rep. of Germany

[21] Appl. No.: 28,928

[22] Filed: Apr. 10, 1979

Related U.S. Application Data

[63] Continuation of Ser. No. 819,414, Jul. 26, 1977, abandoned.

[30] Foreign Application Priority Data

Jul. 29, 1976 [DE] Fed. Rep. of Germany ....... 2634455

[51] Int. Cl.³ .................. A01N 37/00; A01N 37/44; C07C 125/067
[52] U.S. Cl. ......................................... 71/106; 71/111; 560/27; 560/28; 560/29; 560/31; 560/32; 560/115; 560/133
[58] Field of Search .................. 71/106, 111; 560/132, 560/136, 24, 28, 30, 27, 29, 31, 32, 115, 117, 118, 133; 424/300

[56] References Cited

U.S. PATENT DOCUMENTS

| | | | |
|---|---|---|---|
| 3,434,822 | 3/1969 | Wilson et al. | 560/136 |
| 4,013,450 | 3/1977 | Olin et al. | 71/111 |

FOREIGN PATENT DOCUMENTS 1518815  4/1969  Fed. Rep. of Germany .

*Primary Examiner*—Natalie Trousof
*Assistant Examiner*—L. Hendriksen
*Attorney, Agent, or Firm*—Michael J. Striker

[57] ABSTRACT

Carbamic acid ester of the formula

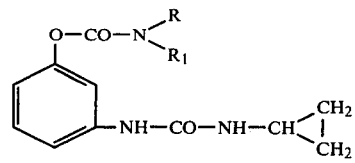

in which R and $R_1$ are the same or different and are hydrogen, an aliphatic hydrocarbon residue which may also be substituted, a cycloaliphatic hydrocarbon residue which may also be substituted, an aromatic hydrocarbon residue which may also be substituted or a heterocyclic residue or wherein R and $R_1$ together with the adjoining nitrogen atom form a heterocyclic residue.

The compounds of the invention are herbicidal agents of particularly strong activity.

27 Claims, No Drawings

CARBAMIC ACID ESTER, PROCESS FOR MAKING THE SAME AND COMPOSITION CONTAINING SAME

This is a continuation of application Ser. No. 819,414, filed July 26, 1977 now abandoned.

BACKGROUND OF THE INVENTION

This invention relates to carbamic acid (3-(3-cyclopropylureido)-phenyl)-esters.

The herbicidal activity of carbamic acid (3-3-alkylureido)-phenyl-esters has become known by German published application No. 1,518,815. However, the herbicidal activity of these compounds is not always adequate.

It is therefore an object of the present invention to provide for a herbicidal agent which has a substantially higher activity.

This object is met by a herbicidal agent which comprises at least one compound of the formula

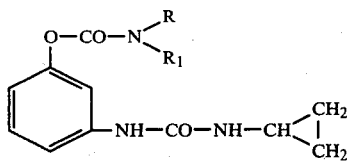

in which R and $R_1$ are the same or different and are hydrogen, an aliphatic hydrocarbon residue which may also be substituted, a cycloaliphatic hydrocarbon residue which may also be substituted, an aromatic hydrocarbon residue which may also be substituted or a heterocyclic residue or wherein R and $R_1$ together with the adjoining nitrogen atom form a heterocyclic residue.

The compounds of the invention have strong herbicidal activities and surpass in this regard surprisingly compounds of an analogous constitution and similar applications as disclosed in the prior art. They also have a valuable combination of selectivity and herbicidal activity.

The compounds of the invention are characterized by a broad herbicidal activity when applied to the ground and when applied to leaves. They can therefore be used with definite results against mono- and di-cotyl weeds. Their use in view of their selectivity can be effected without prejudice in agricultural plantations, for instance plantations where peanuts, potatoes, rice, peas and any kind of corn (cereals) are grown.

The application can be effected both by preemergence and postemergence use and in this way they can be employed for combatting weeds occurring in the fields such as Sinapis, Stellaria, Senecio, Matricaria, Ipomoea, Chrysanthemum, Lamium, Centaurea, Amaranthus, Alopecurus, Echinochloa, Setaria, Sorghum, Lolium, and other weeds. In their use against seed weeds they are normally employed in amounts between about 0.5 kg of active agent per about 2.5 acres up to about 5 kg of active agent per about 2.5 acres. However, in higher amounts the compounds of the invention can also be used as total herbicides to destroy or suppress a wasteland flora during a full vegetation period.

DISCUSSION OF THE INVENTION AND PREFERENTIAL EMBODIMENTS

The compounds of the invention can either be used alone or in mixture with each other or together with other active agents. Depending on the specific purpose the following herbicidal agents may be used together with the compounds of the invention and may also be added only immediately prior to use of the compounds:

substituted anilines,
substituted aryloxycarboxylic acids and their salts, esters and amides,
substituted ethers,
substituted arsonic acids and their salts, esters and amides,
substituted benzimidazoles,
substituted benzisothiazoles,
substituted benzthiadiazinone dioxides,
substituted benzoxazines,
substituted benzoxazinones,
substituted benzthiazoles,
substituted benzthiadiazine,
substituted biurets,
substituted quinolines,
substituted carbamates,
substituted aliphatic carboxylic acids and their salts, esters and amides,
substituted aromatic carboxylic acids and their salts, esters and amides,
substituted carbamoylalkyl-thio- or dithiophosphates
substituted quinazolines,
substituted cycloalkylamidocarbothiolic acids and their salts, esters and amides,
substituted cycloalkylcarboamido -thiazoles,
substituted dicarboxylic acids and their salts, esters and amides,
substituted dihydrobenzofuranylsulfonates,
substituted disulfides,
substituted dipyridylium salts,
substituted dithiocarbamates,
substituted dithiophosphoric acids and their salts, esters and amides,
substituted urea derivatives,
substituted hexahydro-1H-carbothioates,
substituted hydantoines,
substituted hydrazides,
substituted hydrazonium salts,
substituted isoxazolpyrimidones,
substituted imidazoles,
substituted isothiazolpyrimidones,
substituted ketones,
substituted naphthoquinones,
substituted aliphatic nitriles,
substituted aromatic nitriles,
substituted oxadiazoles,
substituted oxadiazinons,
substituted oxadiazolidinediones,
substituted oxadiazinediones,
substituted phenols and their salts and esters,
substituted phosphonic acids and their salts, esters and amides,
substituted phosphoniumchlorides,
substituted phosphonalkylglycines,
substituted phosphites,
substituted phosphoric acids and their salts, ester and amides,
substituted piperidines,
substituted pyrazoles,
substituted pyrazolalkylcarboxylic acids and their salts, esters, and amides,
substituted pyrazolium salts,
substituted pyrazoliumalkylsulfates, substituted pyridazines,
substituted pyridazones,
substituted pyridine-carboxylic acids and their salts, esters and amides,
substituted pyridines,
substituted pyridinecarboxylates,
substituted pyridinones,
substituted pyrimidones,
substituted pyrrolidine-carboxylic acids and their salts, esters and amides,
substituted pyrrolidines,
substituted arylsulfonic acids and their salts, esters and amides,
substituted styrenes,
substituted tetrahydro-oxadiazindiones,
substituted tetrahydromethanoindenes,
substituted tetrahydro-diazol-thiones,
substituted tetrahydro-thiadiazine-thiones,
substituted tetrahydro-thiadiazolediones,
substituted thiadiazoles,
substituted aromatic thiocarboxylic acid amides,
substituted thiocarboxylic acids and their salts, esters and amides,
substituted thiolcarbamates,
substituted thiophosphoric acids and their salts, esters and amides,
substituted triazines,
substituted triazoles
substituted uracils, and
substituted urethidindiones.

In addition other additives can be used, for instance nonphytotoxic additives which result in a synergistic increase of activity in herbicides such as wetting agents, emulsifying agents, solvents and oily additives.

The agents of the invention or their mixtures are advantageously used in the form of powders, dusting agents, granulates, solutions, emulsions or suspensions in which case liquid and/or solid carrier materials or diluents may be added. If desired there may also be added agents supporting the wetting, adhesion, emulsifying and/or dispersion properties.

Suitable liquid carrier materials are for instance water, aliphatic and aromatic hydrocarbons, such as benzene, toluene, xylene, cyclohexanone, isophorone, dimethylsulfoxide, dimethylformamide and furthermore mineral oil fractions.

As solid carrier materials mineral earths may be used, for instance, tonsil, silica gel, talc, kaolin, attaclay, limestone, silicic acid, and also plant products, for instance, flours.

Surface active agents may be added to the compounds such as calciumlignosulfonate, polyoxyethylenealkyl-phenyl-ethers, naphthalinesulfonic acids and their salts, phenolsulfonic acids and their salts, formaldehyde condensation products, fatty alcohol sulfates as well as substituted benzosulfonic acids and their salts.

The amount of the active agents may be varied widely. For instance, herbicidal compositions may be used containing about 10 to 80% by weight of active agents, about 90 to 20% by weight of liquid or solid carrier materials to which, if desired, up to 20% by weight of surface active agents may be added.

The application of the compounds can be effected in conventional form. For instance the application may be in form of a suspension with water as carrier material in spray amounts of about 100 to 1000 meters per about 2.5 acres. The application can be effected both in so-called "low-volume" and "ultra low-volume" process as well as in the form of so-called microgranulates.

Among the compounds of the invention those have a particularly superior activity in which in the above-given formula R and $R_1$ are hydrogen, alkyl of 1 to 6 carbon atoms, alkenyl of 2 to 6 carbon atoms, alkinyl of 2 to 6 carbon atoms, cycloalkyl of 3 to 6 carbon atoms, phenyl, alkylphenyl wherein the alkyl moiety has 1 to 3 carbon atoms, halogenophenyl, alkoxyphenyl wherein the alkoxy moiety has 1 to 3 carbon atoms, trifluoromethylphenyl, nitrophenyl or naphthyl. The phenyl and the naphthyl group may be the same or different in case of R and $R_1$ and they may be substituted by one or two substituents. A preferred list of groups constituting R and $R_1$ would be the following: methyl, ethyl, propyl, isopropyl, allyl, propinyl, cyclopropyl, butyl, isobutyl, sec.-butyl, tert.-butyl, pentyl, isopentyl, hexyl, cyclohexyl, phenyl, methylphenyl, dimethylphenyl, chlorophenyl, dichlorophenyl, methoxyphenyl, dimethoxyphenyl, trifluoromethylphenyl, nitrophenyl or naphthyl. The phenyl and naphthyl groups may again be the same or may be different in the two cases and they may be substituted again by one or two substituents.

The compounds which so far have not been described in the literature can be made in various ways, for instance, as follows:

I. 1-cyclopropyl-3-(3-hydroxyphenyl)-urea of the formula

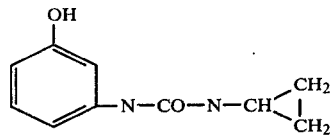

may be reacted in the presence of an acid acceptor with a carbamoylchloride of the formula

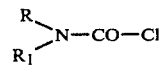

whereupon the reaction product is isolated in conventional form, R and $R_1$ in these cases having the same meaning as in the above formula of the final product.

II. 1-cyclopropyl-3-(3-hydroxyphenyl)-urea of the formula

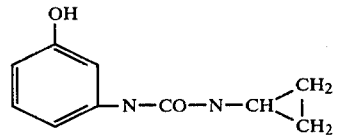

may be reacted with phosgene of the formula

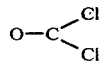

so as to form compounds of the formula

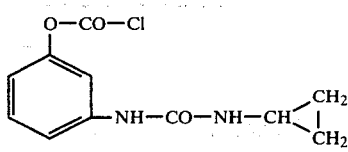

which reaction may be carried out in the presence of an acid acceptor, whereupon the reaction product is then reacted with an amine of the formula

followed by isolation of the reaction product, R and $R_1$ having the same meaning as in the above formula of the final product.

III. 1-cyclopropyl-3-(3-hydroxyphenyl)-urea of the formula

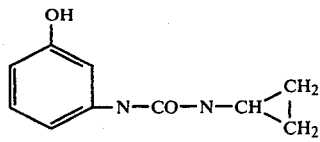

may be reacted with an isocyanate of the formula

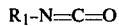

followed by isolation of the reaction product, $R_1$ having the same meaning as in the formula of the final product and R being hydrogen in the final product.

IV. A carbaminic acid-(3-nitrophenyl)-ester of the formula

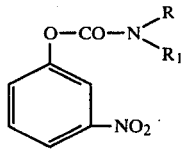

is hydrogenated catalytically, preferably by use of Raney nickel to form the corresponding amine whereupon the amine is then reacted with a cyclopropylisocyanate of the formula

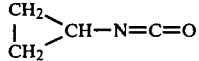

followed by isolation of the reaction product, R and $R_1$ having the same meaning as in the above formula of the final product. As acid acceptors in all these cases can be used the compounds employed conventionally for this purpose. Suited are for instance organic bases such as tertiary amines, for instance triethylamine or N,N-dimethylaniline or a pyridine base, and also suitable inorganic bases such as oxide, hydroxides and carbonates of the alkali- and alkaline earth metals. If liquid organic basis are used they can simultaneously serve as solvents. An excess of the amine in the process identified above as II may likewise be used as acid acceptor.

The starting product in most of these reactions, 1-cyclopropyl-3-(3-hydroxyphenyl)-urea, m.p. 154° C. can easily be made by reacting m-aminophenyl with cyclopropylisocyanate.

The reaction of the components can be effected at temperatures between about 0° C. and 120° C. Preferred is a reaction at room temperature.

For the synthesis the components are used in about equimolar amounts.

Suitable reaction media are solvents which are inert towards the reaction components. As such may be mentioned the following: Aliphatic and aromatic hydrocarbons like petroleum ether, cyclohexane, benzene, toluene and xylene; halogenated hydrocarbons such as methylene chloride, chloroform, carbontetrachloride; halogenated ethylenes; ether-type compounds such as diethylether, tetrahydrofuran and dioxane; ketones like acetone and methylisobutylketone and isophorone, esters like acetic acid methyl and ethyl ester; acid amides such as dimethylformamide and hexamethyl phosphorustriamide; and carboxylic acid nitriles such as acetonitrile and many others.

The isolation of the compounds of the invention is effected in case of compounds of low solubility by filtration, in case of a better solubility by distilling off of the solvent at normal or reduced pressure or by precipitation with less polar organic solvents such as hydrocarbons or ethers like petroleum ether and diisopropylether and others.

The following examples illustrate the making of the compounds of the invention.

EXAMPLE 1

6.6 butylisocyanate and three drops of triethylamine were added by stirring to a solution of 11.5 g of 1-cyclopropyl-3-(3-hydroxyphenyl)-urea in 200 milliliters acetonitrile. A gel-like mass precipitated during standing of the mixture through the night. It was removed by suction and washed with diisopropylether. There were thus obtained 14.0 g (80.3% of the theoretical value) of butylcarbamic acid-(3-(3-cyclopropylureido)-phenyl)-ester having a melting point of 154° C.

Analysis: calculated C 61.84% H 7.27% N 14.42% obtained C 61.78% H 7.68% N 14.61%.

EXAMPLE 2

19.2 g of 1-cyclopropyl-3-(3-hydroxyphenyl)-urea were suspended in 60 ml pyridine and were reacted while being stirred with a suspension of 76.5 g of N-ethyl-N-phenylcarbamoylchloride in 70 ml pyridine. Stirring was continued for 3 hours at 70° C. until a clear solution was obtained. After cooling to room temperature the reaction mass was placed on ice water. The mixture was then acidified with hydrochloric acid and the precipitated compound was extracted with methylene chloride. The organic phase was washed with dilute hydrochloric acid and water and dried on magnesium sulphate. The solvent was distilled off in a vacuum. The remaining residue was recrystallized from diisopropylether.

The yield was 29.7 g (87.6% of the theoretical value) of N-ethyl-N-phenylcarbamic acid-(3-(3-cyclopropylureido)-phenyl)-ester; m.p. 120° C.

Analysis: calculated C 67.24% H 6.24% N 12.38%. obtained C 67.55% H 6.33% N 11.99%.

In an analogous manner the following compounds of the invention were obtained.

| Compound | Physical constants |
|---|---|
| Carbanilic acid-(3-(3-cyclopropyl-ureido)-phenyl)-ester | m.p. 160° C. |
| Methylcarbamic acid-(3-(3-cyclopropyl-ureido)-phenyl)-ester | m.p. 143° C. |
| Ethylcarbamic acid-(3-(3-cyclopropyl-ureido)-phenyl)-ester | m.p. 170° C. |
| Cyclopropylcarbamic acid-(3-(3-cyclopropylureido)-phenyl)-ester | m.p. 184° C. |
| tert.-butylcarbamic acid-(3-(3-cyclopropylureido)-phenyl)-ester | m.p. 137° C. |
| isopropylcarbamic acid-(3-(3-cyclopropylureido)-phenyl)-ester | m.p. 180° C. (decomposition) |
| 3-methylcarbanilic acid-(3-(cyclopropylureido)-phenyl)-ester | m.p. 155° C. |
| Allylcarbamic acid-(3-(3-cyclopropylureido)-phenyl)-ester | m.p. 153° C. |
| Propylcarbamic acid-(3-(3-cyclopropylureido)-phenyl)-ester | m.p. 160° C. |
| Cyclohexylcarbamic acid-(3-(3-cyclopropylureido)-phenyl)-ester | m.p. 182° C. |
| 3-chlorocarbanilic acid-(3-(3-cyclopropylureido)-phenyl)-ester | m.p. 161° C. |
| Dimethylcarbamic acid-(3-(3-cyclopropylureido)-phenyl)-ester | m.p. 118° C. |
| Diallylcarbamic acid-(3-(3-cyclopropylureido)-phenyl)-ester | m.p. 66° C. |
| N-methyl-N-phenylcarbamic acid-(3-(3-cyclopropylureido)-phenyl)-ester | m.p. 155° C. |
| 3-methoxycarbanilic acid-(3-(3-cyclopropylureido)-phenyl)-ester | m.p. 115° C. |
| 3,5-dichlorocarbanilic acid-(3-(3-cyclopropylureido)-phenyl)-ester | m.p. 174° C. |
| Diphenylcarbamic acid-(3-cyclopropylureido)-phenyl)-ester | m.p. 190° C. |
| 3-ntirocarbanilic acid-(3-(3-cyclopropylureido)-phenyl)-ester | m.p. 185° C. |
| 1-naphthylcarbamic acid-(3-(3-cyclopropylureido)-phenyl)-ester | m.p. 187° C. |
| 3-trifluoromethylcarbanilic acid-(3-(3-cyclopropylureido)-phenyl)-ester | m.p. 179° C. |
| 3,4-dichlorocarbanilic acid-(3-(3-cyclopropylureido)-phenyl)-ester | m.p. 179° C. |
| 2-methylcarbanilic acid-(3-(3-cyclopropylureido)-phenyl)-ester | m.p. 170° C. |

The compounds of the invention are colorless and have no smell. They are crystalline substances which are insoluble in water and nonpolar organic solvents such as hydrocarbons. They have a low solubility in ether, ketones, esters, carbonitriles and alcohols. Their solubility is high in polar organic solvents such as dimethylsulfoxide, dimethylformamide and lower carboxylic acids.

USES AND APPLICATION

The following examples will illustrate the use and activity of the compounds of the invention.

EXAMPLE 3

The compounds listed in the following Table I were applied in a hothouse in preemergence and postemergence sprays in amounts of 5 kg of active agent per about 2.5 acres suspended in 500 liters of water per about 2.5 acres. The test plants were Sinapis and Solanum.

The results were evaluated after 3 weeks on a scale from 0 = no effects to 4 = total destruction of the plants.

As appears from Table I ordinarily a total destruction of the test plants was obtained.

TABLE I

| | Application | | | |
|---|---|---|---|---|
| | Preemergence | | Postemergence | |
| Compound of the Invention | Sinapis | Solanum | Sinapis | Solanum |
| Carbanilic acid-(3-(3-cyclopropylureido)-phenyl)-ester | 4 | 3 | 4 | 4 |
| Methylcarbamic acid-(3-(3-cyclopropylureido)-phenyl)-ester | 4 | 4 | 4 | 4 |
| ethylcarbamic acid-(3-(3-cyclopropylureido)-phenyl)-ester | 4 | 4 | 4 | 4 |
| Cyclopropylcarbamic acid-(3-(3-cyclopropylureido)-phenyl)-ester | 4 | 4 | 4 | 4 |
| tert.-butylcarbamic acid-(3-(3-cyclopropylureido)-phenyl)-ester | 4 | 4 | 4 | 4 |
| Isopropylcarbamic acid-(3-(3-cyclopropylureido)-phenyl)-ester | 4 | 4 | 4 | 4 |
| 3-methylcarbamic acid-(3-(3-cyclopropylureido)-phenyl)-ester | 4 | 4 | 2 | 4 |
| Allylcarbamic acid-(3-(3-cyclopropylureido)-phenyl)-ester | 4 | 4 | 4 | 4 |
| Propylcarbamic acid-(3-(3-cyclopropylureido)-phenyl)-ester | 4 | 4 | 4 | 4 |
| Butylcarbamic acid-(3-(3-cyclopropylureido)-phenyl)-ester | 4 | 4 | 4 | 4 |
| Cyclohexylcarbamic acid-(3-(3-cyclopropylureido)-phenyl)-ester | 4 | 4 | 4 | 4 |
| 3-chlorocarbanilic acid-(3-(3-cyclopropylureido)-phenyl)-ester | 0 | 4 | 1 | 4 |
| Dimethylcarbamic acid-(3-(3-cyclopropylureido)-phenyl)-ester | 4 | 4 | 4 | 4 |
| Diallylcarbamic acid-(3-(3-cyclopropylureido)-phenyl) ester | 4 | 4 | 4 | 4 |
| N-methyl-N-phenylcarbamic-acid-(3-(3-cyclopropylureido)-phenyl)-ester | 4 | 4 | 4 | 4 |
| 3-methoxycarbanilic acid (3-(3-cyclopropylureido)-phenyl)-ester | 4 | — | 4 | 3 |
| N-(2-cyanethyl)-carbanilic acid-(3-(3-cyclopropylureido)-phenyl)-ester | 4 | 4 | 4 | 4 |

EXAMPLE 4

The plants listed in the following Table II were treated in a hothouse with the also indicated compounds in a preemergence application in amounts of 3 kg of active agent per about 2.5 acres. The comparison compound was N-propyl-(N'-(3-N''-methylcarbamoyloxy)-phenyl)-urea.

The plants were in the growing stage. The compounds were applied as suspensions in water amounts corresponding to 500 liters per 2.5 acres.

The results were evaluated after 14 days on a scale reaching from 0=total destruction to 10=no injury to the plants.

The results shown in Table II illustrate the high compatibility of the compounds of the invention with agricultural plants while on the other hand the comparison compound did not have a sufficient herbicidal activity.

TABLE II

REEMERGENCE APPLICATION

| | Peanuts | Potatoes | Peas | Rice | Stellaria | Senacio | Matricaria | Lamium | Centaurea | Amaranthus |
|---|---|---|---|---|---|---|---|---|---|---|
| Compounds of the Invention | | | | | | | | | | |
| Methylcarbamic acid-(3-(3-cyclopropylureido)-phenyl)-ester | 10 | 8 | — | 7 | 0 | 0 | 0 | 0 | 0 | 0 |
| Ethylcarbamic acid-(3-(3-cyclopropylureido)-phenyl)-ester | 10 | 9 | — | 10 | 0 | 0 | 0 | 0 | 0 | 0 |
| Cyclopropylcarbamic acid-(3-(3-cyclopropylureido)-phenyl)-ester | 10 | 10 | 10 | 10 | 0 | 0 | 0 | 0 | 0 | 0 |
| tert.-butylcarbamic acid-(3-(3-cyclopropylureido)-phenyl)-ester | 10 | 10 | — | 8 | 0 | 0 | 0 | 0 | 0 | 0 |
| Isopropylcarbamic acid-(3-(3-cyclopropylureido)-phenyl)-ester | 10 | 10 | — | — | 0 | 0 | 0 | 0 | 0 | 0 |
| Allylcarbamic acid-(3-(3-cyclopropylureido)-phenyl)-ester | 10 | 10 | 10 | — | 0 | 0 | 0 | 0 | 0 | 0 |
| Propylcarbamic acid-(3-(3-cyclopropylureido)-phenyl)-ester | 10 | 8 | — | — | 0 | 0 | 0 | 0 | 0 | 0 |
| Butylcarbamic acid-(3-(3-cyclopropylureido)-phenyl)-ester | 10 | 8 | 10 | 8 | 0 | 0 | 0 | 0 | 0 | 0 |
| Comparison compound (German published application 1518815) N-propyl-(N'-(3-N"-methyl-carbamoyloxy)-phenyl-urea | 10 | 10 | 9 | 10 | 1 | 0 | 0 | 0 | 1 | 6 |
| Untreated (control) | 10 | 10 | 10 | 10 | 10 | 10 | 10 | 10 | 10 | 10 |

| | Chrysanthemum | Ipomea | Avena | Alopecurus | Echinochloa | Setaria | Digitaria | Sorghum | Poa |
|---|---|---|---|---|---|---|---|---|---|
| Compounds of the Invention | | | | | | | | | |
| Methylcarbamic acid-(3-(3-cyclopropylureido)phenyl)-ester | 0 | 0 | 0 | 2 | 3 | 0 | 0 | 2 | 4 |
| Ethylcarbamic acid-(3-(3-cyclopropylureido)-phenyl)-ester | 0 | 0 | 0 | 2 | 2 | 0 | 0 | 1 | 1 |
| Cyclopropylcarbamic acid-(3-(3-cyclopropylureido)-phenyl)-ester | 0 | 0 | 0 | 1 | 1 | 0 | 0 | 0 | 2 |
| tert.-butylcarbamic acid-(3-(3-cyclopropylureido)-phenyl)-ester | 0 | 0 | 0 | 0 | 0 | 0 | 0 | 1 | 0 |
| Isopropylcarbamic acid-(3-(3-cyclopropylureido)-phenyl)-ester | 0 | 0 | 0 | 0 | 0 | 0 | 0 | 0 | 0 |
| Allylcarbamic acid-(3-(3-cyclopropylureido)-phenyl)-ester | 0 | 0 | 0 | 1 | 1 | 0 | 0 | 3 | 1 |
| Propylcarbamic acid-(3-(3-cyclopropylureido)-phenyl)-ester | 0 | 0 | 0 | 0 | 0 | 0 | 0 | 0 | 0 |
| Butylcarbamic acid-(3-(3-cyclopropylureido)-phenyl)-ester | | | | | | | | | |
| Comparison compound (German published application 1518815) N-propyl-(N'-(3-N"-methyl-carbamoyloxy)-phenyl)-urea | 0 | 0 | 3 | 7 | 7 | 9 | 7 | 9 | 8 |
| Untreated (control) | 10 | 10 | 10 | 10 | 10 | 10 | 10 | 10 | 10 |

EXAMPLE 5

The plants listed in the following Table III were treated in a postemergence application with the compounds likewise indicated in the Table in a hothouse in amounts of 3 kg of active agent per about 2.5 acres. The comparison compound was N-propyl-(N'-(3-N"-methylcarbamoyloxy)-phenyl)-urea.

The plants were in the growing stage. The compounds were apllied as suspensions in water corresponding to 500 liters per 2.5 acres.

The results were evaluated after 14 days on a scale from 0=total destruction to 10=no injury to the plants.

The values in Table III demonstrate the high compatibility with agricultural plants and the good herbicidal action of the compounds of the invention while on the other hand the comparison compound of the prior art did not have a sufficient herbicidal activity.

TABLE III

POSTEMERGENCE APPLICATION

| | Peanuts | Potatoes | Peas | Rice | Stellaria | Senacio | Matricaria | Lamium | Centaurea | Amaranthus |
|---|---|---|---|---|---|---|---|---|---|---|
| Compounds of the Invention | | | | | | | | | | |
| Methylcarbamic acid-(3-(3-cyclopropylureido)-phenyl)-ester | 10 | 7 | — | — | 0 | 0 | 0 | 0 | 0 | 0 |
| Ethylcarbamic acid-(3-(3-cyclopropylureido)-phenyl)-ester | 10 | 7 | 7 | — | 0 | 0 | 0 | 0 | 0 | 0 |
| Cyclopropylcarbamic acid-(3-(3-cyclopropylureido)-phenyl)-ester | 10 | 8 | 10 | 7 | 0 | 0 | 0 | 0 | 1 | 0 |
| tert.-butylcarbamic acid-(3-(3-cyclopropylureido)-phenyl)-ester | 10 | — | 8 | 0 | 0 | 0 | 0 | 0 | 0 | 0 |

TABLE III-continued

POSTEMERGENCE APPLICATION

| | | | | | | | | | | |
|---|---|---|---|---|---|---|---|---|---|---|
| Isopropylcarbamic acid-(3-(3-cyclopropylureido)-phenyl)-ester | 10 | 8 | 5 | — | 0 | 0 | 0 | 0 | 0 | 0 |
| Allylcarbamic acid-(3-(3-cyclopropylureido)-phenyl)-ester | 10 | 7 | 10 | 10 | 0 | 0 | 0 | 0 | 0 | 0 |
| Propylcarbamic acid-(3-(3-cyclopropylureido)-phenyl)-ester | 10 | — | 8 | 8 | 0 | 0 | 0 | 0 | 0 | 0 |
| Butylcarbamic acid-(3-(3-cyclopropylureido)-phenyl)-ester | 10 | 8 | 8 | 8 | 0 | 0 | 0 | 0 | 0 | 0 |
| Cyclohexylcarbamic acid-(3-(3-cyclopropylureido)-phenyl)-ester | 10 | 10 | 10 | 10 | 0 | 0 | 0 | 0 | 0 | 0 |
| 3-methylcarbamic acid-(3-(3-cyclopropylureido)-phenyl)-ester | 10 | 10 | 10 | 10 | 0 | 0 | 0 | 0 | 0 | 0 |
| Comparison compound | | | | | | | | | | |
| (German published application 1,518,815) | | | | | | | | | | |
| N-propyl-(N'-(3-N''-methyl-carbamoyloxy)-phenyl)-urea | 10 | 10 | 10 | 10 | 1 | 0 | 0 | 0 | 4 | 4 |
| Untreated (control) | 10 | 10 | 10 | 10 | 10 | 10 | 10 | 10 | 10 | 10 |

| | Chrysanthemum | Ipomea | Avena | Alopecurus | Echinochloa | Setaria | Digitaria | Sorghum | Poa |
|---|---|---|---|---|---|---|---|---|---|
| Compounds of the invention | | | | | | | | | |
| Methylcarbamic acid-(3-(3-cyclopropylureido)-phenyl)-ester | 0 | 0 | 0 | 0 | 0 | 0 | 0 | 0 | 0 |
| Ethylcarbamic acid-(3-(3-cyclopropylureido)-phenyl)-ester | 0 | 0 | 0 | 0 | 0 | 0 | 0 | 0 | 0 |
| Cyclopropylcarbamic acid-(3-(3-cyclopropylureido)-phenyl)-ester | 0 | 0 | 0 | 1 | 0 | 0 | 0 | 0 | 1 |
| tert.-butylcarbamic acid-(3-(3-cyclopropylureido)-phenyl)-ester | 0 | 0 | 1 | 0 | 0 | 0 | 0 | 0 | 0 |
| Isopropylcarbamic acid-(3-(3-cyclopropylureido)-phenyl)-ester | 0 | 0 | 0 | 0 | 0 | 0 | 0 | 0 | 0 |
| Allylcarbamic acid-(3-(3-cyclopropylureido)-phenyl)-ester | 0 | 0 | 2 | 1 | 0 | 0 | 0 | 4 | 3 |
| Propylcarbamic acid-(3-(3-cyclopropylureido)-phenyl)-ester | 0 | 0 | 0 | 0 | 0 | 0 | 0 | 0 | 0 |
| Butylcarbamic acid-(3-(3-cyclopropylureido)-phenyl)-ester | 0 | 0 | — | 2 | 0 | 0 | 0 | 3 | 0 |
| Cyclohexylcarbamic acid-(3-(3-cyclopropylureido)-phenyl)-ester | 0 | 0 | — | 2 | 3 | 0 | 3 | — | 3 |
| 3-methylcarbamic acid-(3-(3-cyclopropylureido)-phenyl)-ester | 0 | 0 | — | — | 1 | 0 | 0 | — | 2 |
| Comparison compound | | | | | | | | | |
| (German published application 1,518,815) | | | | | | | | | |
| N-propyl-(N'-(3-N''-methyl-carbamoyloxy)-phenyl)-urea | 0 | 0 | 5 | 6 | 6 | 8 | 8 | 10 | 7 |
| Untreated (control) | 10 | 10 | 10 | 10 | 10 | 10 | 10 | 10 | 10 |

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A compound of the formula

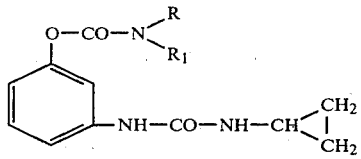

wherein R and $R_1$ are the same or different and are selected from the group consisting of hydrogen, alkyl of 1 to 6 carbon atoms, alkenyl of 2 to 6 carbon atoms, alkinyl of 2 to 6 carbon atoms, cycloalkyl of 3 to 6 carbon atoms, phenyl optionally substituted in one or two places by halogen, trifluoromethyl, nitro, alkoxy of one to 3 carbon atoms or alkyl of one to 3 carbon atoms, and naphthyl.

2. The compound of claim 1 which is butylcarbamic acid-(3-(3-cyclopropylureido)-phenyl)-ester.

3. The compound of claim 1 which is N-ethyl-N-phenylcarbamic acid-(3-(3-cyclopropylureido)-phenyl)-ester.

4. The compound of claim 1 which is carbanilic acid-(3-(3-cyclopropylureido)-phenyl)-ester.

5. The compound of claim 1 which is methylcarbamic acid-(3-(3-cyclopropylureido)-phenyl)-ester.

6. The compound of claim 1 which is ethylcarbamic acid-(3-(3-cyclopropylureido)-phenyl)-ester.

7. The compound of claim 1 which is cyclopropylcarbamic acid-(3-(3-cyclopropylureido)-phenyl)-ester.

8. The compound of claim 1 which is tert.-butylcarbamic acid-(3-(3-cyclopropylureido)-phenyl)-ester.

9. The compound of claim 1 which is isopropylcarbamic acid-(3-(3-cyclopropylureido)-phenyl)-ester.

10. The compound of claim 1 which is 3-methylcarbanilic acid-(3-(3-cyclopropylureido)-phenyl)-ester.

11. The compound of claim 1 which is allylcarbamic acid-(3-(3-cyclopropylureido)-phenyl)-ester.

12. The compound of claim 1 which is propylcarbamic acid-(3-(3-cyclopropylureido)-phenyl)-ester.

13. The compound of claim 1 which is cyclohexylcarbamic acid-(3-(3-cyclopropylureido)-phenyl)-ester.

14. The compound of claim 1 which is 3-chlorocarbanilic acid-(3-(3-cyclopropylureido)-phenyl)-ester.

15. The compound of claim 1 which is dimethylcarbamic acid-(3-(3-cyclopropylureido)-phenyl)-ester.

16. The compound of claim 1 which is diallylcarbamic acid-(3-(3-cyclopropylureido)-phenyl)-ester.

17. The compound of claim 1 which is diphenylcarbamic acid-(3-(3-cyclopropylureido)-phenyl)-ester.

18. The compound of claim 1 which is 3-nitrocarbanilic acid-(3-(3-cyclopropylureido)-phenyl)-ester.

19. The compound of claim 1 which is 1-naphthylcarbamic acid-(3-(3-cyclopropylureido)-phenyl)-ester.

20. The compound of claim 1 which is 3-trifluoromethylcarbanilic acid-(3-(3-cyclopropylureido)-phenyl)-ester.

21. The compound of claim 1 which is 3,4-dichlorocarbanilic acid-(3-(3-cyclopropylureido)-phenyl)-ester.

22. The compound of claim 1 which is 2-methylcarbanilic acid-(3-(3-cyclopropylureido)-phenyl)-ester.

23. The compound of claim 1 which is N-methylN-phenylcarbamic acid-(3-(3-cyclopropylureido)-phenyl)-ester.

24. The compound of claim 1 which is 3-methoxycarbanilic acid-(3-(3-cyclopropylureido)-phenyl)-ester.

25. The compound of claim 1 which is 3,5-dichlorocarbanilic acid-(3-(3-cyclopropylureido)-phenyl)-ester.

26. A herbicidal composition comprising about 10 to 80% by weight of at least one active agent as defined in claim 1 and the remainder a liquid or solid carrier material.

27. The composition of claim 26 which additionally includes up to 20% by weight of surface active agents.

* * * * *